(12) United States Patent
Ober et al.

(10) Patent No.: US 9,259,759 B2
(45) Date of Patent: Feb. 16, 2016

(54) PATTERNING OF BIOMATERIALS USING FLUORINATED MATERIALS AND FLUORINATED SOLVENTS

(75) Inventors: Christopher Ober, Ithaca, NY (US); Jin-Kyun Lee, Incheon (KR); Priscilla G. Taylor, Berkeley, CA (US)

(73) Assignee: Cornell University, Ithaca, NY (US)

(*) Notice: Subject to any disclaimer, the term of this patent is extended or adjusted under 35 U.S.C. 154(b) by 372 days.

(21) Appl. No.: 13/582,082

(22) PCT Filed: Mar. 1, 2011

(86) PCT No.: PCT/US2011/026651
§ 371 (c)(1),
(2), (4) Date: Jan. 14, 2013

(87) PCT Pub. No.: WO2011/109368
PCT Pub. Date: Sep. 9, 2011

(65) Prior Publication Data
US 2013/0115430 A1    May 9, 2013

Related U.S. Application Data

(60) Provisional application No. 61/309,052, filed on Mar. 1, 2010.

(51) Int. Cl.
*B05D 1/32* (2006.01)
*G03F 7/004* (2006.01)
*G03F 7/30* (2006.01)
(Continued)

(52) U.S. Cl.
CPC ............... *B05D 1/322* (2013.01); *C12N 11/00* (2013.01); *G03F 7/004* (2013.01); *G03F 7/20* (2013.01); *G03F 7/30* (2013.01); *Y10T 428/24802* (2015.01)

(58) Field of Classification Search
CPC .......... B05D 1/322; C12N 11/00; G03F 7/20
USPC ...................................... 428/195.1
See application file for complete search history.

(56) References Cited

U.S. PATENT DOCUMENTS 4,789,804 A * 12/1988 Karube et al. ................. 310/311
4,859,538 A    8/1989 Ribi
(Continued)

FOREIGN PATENT DOCUMENTS

| WO | 2005108615 A2 | 11/2005 |
| WO | 2007041340 A2 | 4/2007 |
| WO | 2009/126916 A2 | 10/2009 |

OTHER PUBLICATIONS

Lee et al., Protein patterning on silicon-based surface using background hydrophobic thin film, Biosensors & Bioelectronics, 2003, pp. 437-444, 18(4).

(Continued)

*Primary Examiner* — Gerard Higgins
(74) *Attorney, Agent, or Firm* — Hodgson Russ LLP

(57) ABSTRACT

A method for patterning biomaterials is presented. The biomaterials exhibit biological activity after patterning. The use of bio-compatible imaging materials and solvents allows conventional lithographic patterning methods to be applied to patterning biomolecules. The method allows deposition of multiple layers without subsequent layers affecting earlier laid deposits and can pattern multiple different biomolecules on a single surface.

17 Claims, 7 Drawing Sheets

(51) Int. Cl.
*C12N 11/00* (2006.01)
*G03F 7/20* (2006.01)

(56) References Cited

U.S. PATENT DOCUMENTS

| | | | |
|---|---|---|---|
| 7,749,921 | B2 | 7/2010 | Mino et al. |
| 8,846,301 | B2 | 9/2014 | Ober et al. |
| 2005/0037276 | A1 | 2/2005 | Argitis et al. |
| 2006/0063207 | A1 | 3/2006 | Lin et al. |
| 2008/0233489 | A1 | 9/2008 | Blanchet et al. |
| 2009/0305437 | A1 | 12/2009 | Allemand et al. |
| 2010/0048428 | A1 | 2/2010 | Coyer et al. |
| 2010/0289019 | A1 | 11/2010 | Katz et al. |
| 2012/0305897 | A1 | 12/2012 | Ober et al. |
| 2014/0205818 | A1 | 7/2014 | Schwartz et al. |

OTHER PUBLICATIONS

Blawas & Richert, Protein Patterning, Biomaterials, 1998, pp. 595-609, vol. 19.

Escalante, Nanofabrication of Bioinspired Architectures with Light Harvesting Proteins, 2009, pp. 1-189, Wöhrmann Print Service.

Folch & Toner, Microengineering of Cellular Interactions, Annual Review Biomedical Engineering, 2000, pp. 227-256, 02.

Guo, L.J., Recent progress in nanoimprint technology and its applications, J. Phys. D: Appl. Phys., 2004, R123-R141, vol. 37.

Li et al., Biology on a Chip: Microfabrication for Studying the Behavior of Cultured Cells, Crit Rev Biomed Eng, 2003, pp. 423-488, 31(0).

Perl et al., Microcontact Printing: Limitations and Achievements, Advanced Materials, 2009, pp. 2257-2268, 21.

Sorribas et al., Photolithographic generation of protein micropatterns for neuron culture applicatons, Biomaterials, 2002, pp. 893-900, 23.

Tan et al., Simple Approach to Micropattern Cells on Common Culture Substrates by Tuning Substrate Wettability, Tissue Engineering, 2004, pp. 865-872, vol. 10, No. 5/6.

\* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: probe

<400> SEQUENCE: 1
ctgaacggta gcatcttgga                                              20

<210> SEQ ID NO 2
<211> LENGTH: 20
<212> TYPE: DNA
<213> ORGANISM: artificial sequence
<220> FEATURE:
<223> OTHER INFORMATION: Probe

<400> SEQUENCE: 2
tccaagatgc taccgttcag                                              20
```

PATTERNING OF BIOMATERIALS USING FLUORINATED MATERIALS AND FLUORINATED SOLVENTS

CROSS-REFERENCE TO RELATED APPLICATIONS

This application claims priority to U.S. provisional patent application No. 61/309,052 filed Mar. 1, 2010, the disclosure of which is incorporated herein by reference.

STATEMENT REGARDING FEDERALLY SPONSORED RESEARCH

This invention was made with Government support under Grant Number DMR-0602821 awarded by the National Science Foundation. The United States Government has certain rights in the invention.

FIELD OF THE INVENTION

The present invention relates to methods of patterning biomaterials using biologically-compatible fluorinated materials and solvents.

BACKGROUND OF THE INVENTION

Tremendous advances have recently been made in the field of bioelectronics. Biosensors, biological microelectromechanical systems (bio-MEMs) and microfluidic devices are revolutionizing biological and medical research. Similarly, the development of biomolecular arrays and regenerative therapies are enabling unprecedented studies in fundamental biology and applications in tissue engineering, respectively.

The ability to define multiple biomolecules on a single surface while retaining their functionality is integral to the development of, for example, bio-devices, for biomolecule microarrays and in tissue engineering. Consequently, multicomponent patterning of biomolecules has become an active area of research. Patterning techniques for single component patterning have been extensively developed. However, multicomponent patterning introduces unique challenges, which have yet to be satisfactorily addressed. Multicomponent protein patterning requires the ability to define multiple biomolecules on a single substrate while avoiding nonspecific binding and retaining biomolecule integrity. All of these issues must be addressed in evaluating a patterning method.

Techniques using photolithography, soft-lithography, dip-pen lithography, and spot-arraying have all been explored and represent the principal advances in the field of multicomponent protein patterning. Photolithography is a mature patterning technique that is promising for biomolecule applications as it allows for high-resolution and precise alignment, and is a high-throughput process. The greatest disadvantage of photolithography is that it traditionally requires harsh photoresists and developers as well as heating, which often leads to denaturation of delicate biomolecules. Many clever strategies have been developed to circumvent these requirements. However, these strategies are necessarily specialized and lack universal applicability.

Soft-lithography is an inexpensive and parallel patterning process, which also has the ability to produce three-dimensional structures. However, due to the elastomeric nature of the stamps, mechanical deformation necessarily occurs and results in pattern deformation. Furthermore, soft-lithography is limited by lack of registration capabilities. Dip-pen lithography offers the ability to precisely place nanoscale arrays of proteins; though, by nature, this technique proves to be prohibitively time-consuming. Spot-arraying techniques, including ink-jet printing, are able to generate arrays with spot sizes close to 100 µm. Although this can be a very cost-effective method, resolution is too low to be practical for many applications.

Conventional lithographic patterning methods are attractive for this application, but the fact that they require the use of organic solvents and imaging materials, which are in general damaging to fragile biomolecules, is considered a technical bottleneck. Preserving the integrity of proteins during the patterning process and non-specific binding remain significant challenges to be overcome. In particular, the issue of binding multiple proteins to a single surface has yet to be satisfactorily addressed, despite substantial research on the subject. Based on the foregoing, there exists an ongoing and unmet need for a method of patterning biomaterials, and in particular making multiple overlaid patterns of biomaterials.

BRIEF SUMMARY OF THE INVENTION

In an aspect, the present invention provides a method for making a pattern of biomolecules selected from the group consisting of peptides, polypeptides, proteins, polynucleotides and combinations thereof comprising the steps of: a) forming a pattern of a fluorinated organic material on a surface of a substrate such that a first portion of the substrate is covered by the fluorinated organic materials and a second portion of the substrate is not covered by the fluorinated organic material; b) depositing the biomolecules on the patterned substrate from a) thereby associating the biomolecules with at least the second portion of the substrate; and c) removing the fluorinated organic material and the biomolecules associated therewith thereby forming a pattern of the biomolecules associated with the substrate, wherein the biomolecules exhibit at least one biological activity. In an embodiment, the method further comprises the step of repeating steps a), b) and c) to generate a plurality of patterns of the biomolecules on the substrate. For example, the repeating step can be carried out from 1 to 10 times, including all integers therebetween.

In an embodiment, the fluorinated has at least 25% by weight fluorine. In an embodiment, the fluorinated organic material is a fluorinated organic polymer. In an embodiment, the fluorinated organic material is deposited by spin-coating using a solution of the fluorinated organic polymer in a fluorinated organic solvent. In an embodiment, the forming a pattern step is carried out by imprint lithography or photolithography.

In an embodiment, the biomaterial is a protein. In another embodiment, the protein is an antibody or antigen binding fragment thereof. In an embodiment, intact cells or cell extracts are deposited on the protein after deposition of the protein.

In an embodiment, the fluorinated organic material and the associated biomolecules are selectively removed from the substrate by contacting the substrate from with a fluorinated solvent. In an embodiment, the fluorinated solvent is a hydrofluoroether.

In an embodiment, the pattern is formed by imprint lithography and the substrate is then contacted with an argon/oxygen plasma to remove residual fluorinated organic material that is not part of the pattern of fluorinated organic material.

In an aspect, the present invention provides a pattern of biomaterial or a plurality of biomaterials on a substrate formed by a method of the present invention. In another aspect, the present invention provides a device comprising a pattern of biomaterial or a plurality of biomaterials on a substrate formed by a method of the present invention. In an embodiment, the device is an organic electronic device.

DETAILED DESCRIPTION OF THE INVENTION

Figure 1:
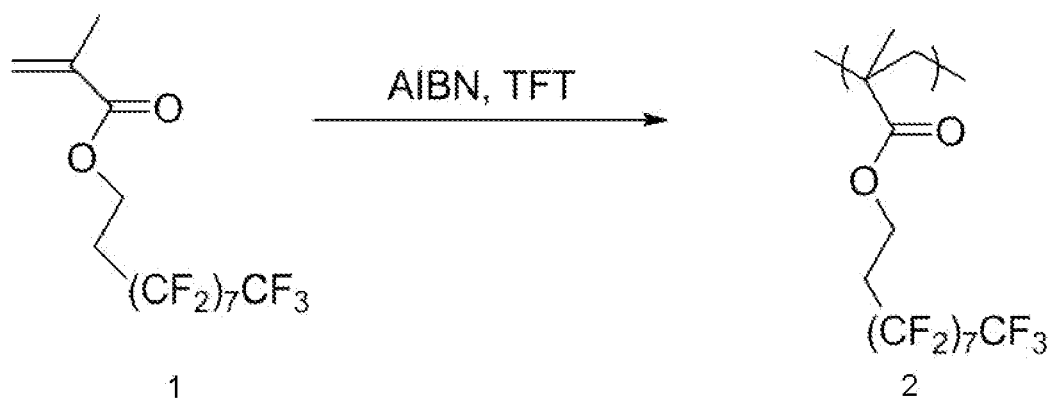
FIG. 1. Synthesis of Imprint Resist 5-1.

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that changes including structural, logical, and electrical changes may be made without departing from the scope of the present invention. The following description of example embodiments is, therefore, not to be taken in a limited sense.

The present invention, in an embodiment, provides methods for making a pattern of biomaterials using fluorinated materials and fluorinated solvents. The present invention uses, for example, lithographic patterning methods that use fluorinated organic polymeric materials or fluorinated organic molecules and fluorous solvents including, for example, hydrofluoroethers (HFEs).

A new paradigm in protein patterning which efficiently addresses the common challenges to this goal, including preservation of protein functionality and the ability to pattern multiple proteins on a single substrate, is presented. This goal is accomplished through adapting conventional lithographic methods with bio-compatible processing solvents and imaging materials.

By implementing bio-compatible solvents and tailored imaging materials, lithographic patterning methods can be directly applied to patterning of biomolecules. This processing system is referred to as orthogonal in that subsequent layers may be deposited such that they do not adversely affect previously deposited layers. This process has the distinct advantage of enabling the straightforward patterning of, for example, multiple proteins on the same surface.

In designing FIFE-compatible resists, used in an embodiment of the present invention, it is desirable that the photoresist be soluble in the fluorous solvents. In general, highly fluorinated solvents dissolve highly fluorinated materials. Therefore a highly fluorinated structure was chosen. Furthermore, it was important that the final structure be simple and free of unnecessary functional groups so that the imaging material would be as inert as possible toward the biomolecules.

The synthesis of fluorinated imaging material (e.g., fluorinated organic polymer and fluorinated organic molecule) soluble in, for example, segregated hydrofluoroethers (HFEs), both of which are benign to biomolecules, are described herein. Patterning by, for example, imprint lithography, which offers high throughput and high resolution as well as registration capabilities, is also described herein. By using imprint lithography, the need for the irradiation used with conventional photolithography, which can be damaging to biomolecules, can be avoided.

In an aspect, the present invention provides a method for making a pattern of biomaterials on a substrate. In an embodiment, the method comprises the steps of: a) forming a pattern of fluorinated organic materials on a surface of a substrate such that a first portion of the substrate is covered by the fluorinated organic materials and a second portion of the substrate is not covered by the fluorinated organic materials; b) depositing the biomaterials on the patterned substrate thereby associating the biomaterials with the fluorinated organic material or the substrate; c) removing the fluorinated organic material, including the biomaterials associated therewith, to provide a pattern of biomaterials associated with the substrate, where the biomolecules exhibit at least one biological activity. In an embodiment, steps a), b) and c) are repeated to generate a plurality of patterns of the same or different biomaterials formed on the substrate. In an embodiment, the repeating step is carried out from 1 to 10 times, including all integers from 1 to 10.

In this embodiment, the first portion of the substrate covered by the fluorinated organic materials may be made up of more than one contiguous or non-contiguous areas. Similarly, the second portion of the substrate not covered by the fluorinated organic materials may be made up of more than one contiguous or non-contiguous areas. In an embodiment, areas of first and second portions may alternate along the length and/or width of the substrate.

The term "biomaterials" (also referred to as biological material) as used herein means a biomolecule (biological molecule) such as, for example, peptides, polypeptides, proteins, polynucleotides, intact cells or cell extracts and combinations thereof. Examples of proteins include, but are not limited to, antibodies and antigen binding fragments thereof. Examples of polynucleotides include, but are not limited to, DNA and RNA. In an embodiment, biomaterials is a composition comprising a biomolecule.

As used herein, the terms "peptide", "polypeptide" and "protein" are used interchangeably herein to mean a molecule comprising two or more amino acids joined to each other by peptide bonds or modified peptide bonds. Polypeptide refers to both short chains, commonly referred to as peptides, glycopeptides or oligomers, and to longer chains, generally referred to as proteins. Polypeptides may contain natural and/or non natural amino acids. Polypeptides include amino acid sequences modified either by natural processes, such as post-translational processing, or by chemical modification techniques that are well known in the art.

As used herein, the term "antibody" means a polypeptide comprising a framework region from an immunoglobulin gene or fragments thereof that specifically binds and recognizes an antigen, and includes whole antibodies, including single-chain whole antibodies, and antigen-binding fragments thereof. The term "antibody" also includes bispecific antibodies, multispecific antibodies and chimeric antibodies provided they exhibit the desired biological activity or function.

The biomaterials associated with the substrate, also referred to herein as "associated biomaterials", preferably retain biological activity after being associated with the substrate. Retained biological activity can be evidenced according to parameters that will be apparent to those skilled in the art depending on the type of associated biomaterials. In an embodiment, the associated biomolecule is a protein or complex of proteins that has, for instance, enzymatic activity and will retain the same or similar enzymatic activity as it had prior to being associated. Thus, an enzyme that facilitates conversion of one or more enzymatic substrates into one or more products in an in vivo or in vitro environment will retain the ability to facilitate conversion of those one or more enzymatic substrates into those one or more products, although reaction kinetics may be different as compared to the non-associated form of the enzyme. In another embodiment, the associated biological molecule can be an antibody which retains its biological activity insofar as it can specifically recognize the antigen to which it is directed. In another embodiment, the associated biological molecule can be a protein or a peptide which retains its ability to, for example, be recognized by an antibody directed to it, or function as a ligand for a receptor, or as a substrate for an enzyme, etc. In another embodiment, the associated biological molecule is a nucleic acid that retains its ability to, for example, hybridize to a complementary nucleic acid. The nucleic acid may be RNA or DNA. The RNA or DNA can be single or double stranded, and can vary in length and sequence. The nucleic acid can retain its ability to hybridize to a fully or partially complementary nucleic acid, depending on factors well known to those skilled in the art, such as temperature and salt concentrations that affect hybridization stringency. In another embodiment, the associated biomaterial can be intact cells. In this embodiment, the intact cells retain biological activity that is characteristic of their particular cell type. For example, a cell that expresses a particular receptor will continue to express that receptor and the receptor will be able to be bound by its cognate ligand and exhibit the same or similar activity as if the cell was not associated with the substrate.

The term "associated" as used herein refers to interaction between the biomaterials and the fluorinated organic materials or the substrate means the biomaterials are immobilized on the substrate. In various embodiments, the associated biomaterials are immobilized on the substrate as a result of Van der Waals forces, ionic interactions (e.g., formation of an ionic bond or bonds between the biomaterial and the substrate (or substrate having a layer of material which facilitates interaction of the biological material with substrate), or covalent bond between the substrate (or substrate having layer of material which facilitates interaction of the biological material with substrate)).

In an embodiment, the forming comprises the steps of: a) depositing a layer of fluorinated organic material on the substrate; b) patterning the layer of organic material from step b), wherein a first sub-portion of patterned fluorinated organic material and a second sub-portion of patterned fluorinated organic material are formed on the substrate; and c) selectively removing (e.g., by exposure to a suitable solvent) the first sub-portion of patterned fluorinated organic material or the second sub-portion of patterned fluorinated organic material from the substrate, wherein the sub-portion of patterned fluorinated organic material that is not removed is the remaining patterned portion of fluorinated organic material.

The substrate is any material on which a layer of fluorinated organic material (e.g., fluorinated organic polymer or fluorinated organic molecule) can be formed and the layer patterned according to, the present invention. For example, it is desirable the substrate have a smoothness such that a layer of fluorinated organic material, with sufficient uniformity to be patterned, can be formed on the substrate. Also, it is desirable that the fluorinated organic solvent not adversely affect the biological material. The substrate should be compatible with the process steps of the method. Examples of suitable substrates are silicon substrates, glass substrates (e.g., an optical glass substrate) and flexible substrates (e.g., polyimide, polyether ether ketone (PEEK), polyethylene terephthalate (PET)), flexible glass (e.g., Corning® Gorilla® Glass) and the like.

The substrate may, optionally, have a layer of material which facilitates interaction of the biological material with substrate (e.g., immobilizes the biological material on the substrate). For example, a silicon substrate can have a coating of (3-aminopropyl)trimethoxysilane-tetramethoxysilane (APTMS) or aminopropyl-triethoxysilane (APTES). It is considered that the APTMS interacts with a biological material such as a protein to promote binding of the biological material onto the APTMS coated substrate. In an embodiment, a layer of such material is deposited on the substrate. In an embodiment, a protein can facilitates interaction of the biological material with substrate (e.g., immobilizes the biological material on the substrate).

The fluorinated organic material is any material with fluorine content such that the material is soluble in a fluorinated solvent and does not adversely affect the biological molecule. Examples of fluorinated organic materials include, but are not limited to, fluorinated organic polymers (e.g., fluorinated photoresist materials) and fluorinated organic molecules (e.g., molecular glass materials). Also, it is desirable that the material form a layer on the substrate having sufficient uniformity so that the layer can be patterned. The solubility of the material should be at a level that the material can be patterned (e.g., imaged) according to the present method. In various embodiments, the fluorinated organic material has at least 15, 20, 25, 30, 40, 45, 50, 60, 65, 70 or 75% by weight fluorine.

An example of a fluorinated organic molecule is resourcinarene. The resourcinarenes have a pendant alkyl group or alkyl groups. The alkyl groups can have from 1 to 20 carbons, including all integers therebetween. The alkyl group(s) can be substituted (in addition to fluorine substitution) or unsubstituted. Also, the alkyl groups can be branched or unbranched. The alkyl group contains all of the fluorine in the polymer. The alkyl group can be completely fluorinated (i.e., the alkyl group is perfluorinated) or partially fluorinated. In an embodiment, the fluorinated organic molecule is a resourcinarene and has the following structure:

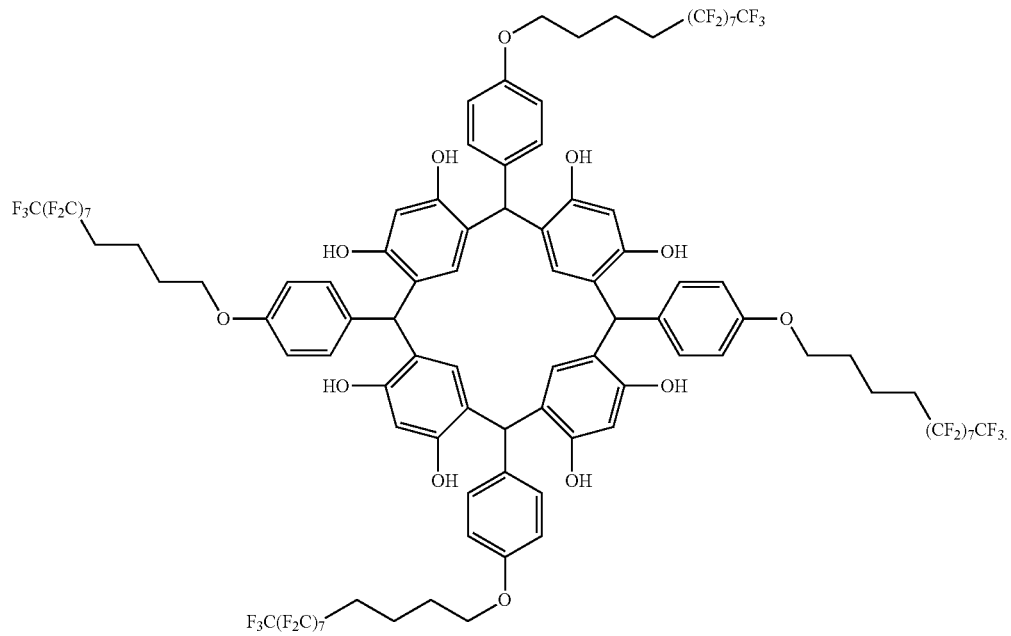

Examples of fluorinated molecular glass photoresists can be found in Dai et al. "Molecular Glass Resists For High Resolution Patterning", Chem. Mater., 18(15): 3404-3411 2006, and De Silva et al. "Molecular Glass Resists as High Resolution Patterning Materials", Adv. Mater., (2008), 20(17), 3355-3361.

Examples of fluorinated organic polymers include, but are not limited to, copolymers of perfluorodecyl methacrylate and 2-nitrobenzyl methacrylate, derivatives thereof, and other polymer photoresists having sufficient fluorine content. In an embodiment, the fluorinated organic polymer has the following structure:

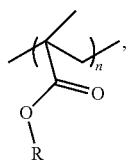

where R is a $C_1$ to $C_{20}$ fluorinated alkyl group and n is an integer from 50 to 2000, including all integers therebeween. The fluorinated alkyl group can be substituted or unsubstituted. The fluorinated alkyl group contains all of the fluorine in the polymer. The fluorinated alkyl group can be completely fluorinated (i.e., the alkyl group is perfluorinated) or partially fluorinated. In another embodiment, the fluorinated organic polymer has the following structure:

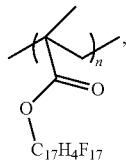

The fluorinated organic material can be deposited by methods well known in the art. For example, the fluorinated organic material can be deposited by spin-coating, dip coating, drop casting, spray coating, inkjet printing, molecular vapor deposition (MVD), and the like. In an embodiment, the fluorinated organic material is deposited by spin-coating using a solution of fluorinated organic polymer in a fluorinated organic solvent.

The fluorinated organic material can be patterned (also referred to as imaging) by methods well known in the art. For example, fluorinated organic material can be patterned by imprint lithography, photolithography, electron beam lithography and the like. In an embodiment, the patterning step provides two complementary patterns in the layer of fluorinated organic material (e.g., a first patterned portion of fluorinated organic material layer and a second patterned portion of fluorinated organic material layer or a first patterned portion of fluorinated organic material and patterned portion of the substrate not covered by the fluorinated organic material). The portions can have different properties such that one portion (e.g., either the first patterned portion of fluorinated organic material layer or the second patterned portion of fluorinated organic material layer) can be selectively removed from the substrate. For example, the portions may have different interaction with (e.g., solubility in) a fluorinated solvent, and one portion can be removed by contacting the patterned fluorinated organic layer on the substrate with a fluorinated solvent. In an embodiment, the forming a patterning step is carried out by imprint lithography or photolithography.

The biomaterial can be deposited on the substrate by a variety of methods. For example, the biomaterial can be deposited by exposing the substrate having a patterned organic material thereon to a solution (e.g., in a suitable buffer solution) comprising the biomaterial.

A variety of biomaterials can be patterned (e.g., a pattern of biomaterials formed) using the methods of the present invention. The biomaterials are not adversely affected by the patterning method of the present invention. By "adversely affected" it is meant that the biomaterials retain the biological activity they had, to the extent that the materials exhibit biological activity, before being subjected to the patterning method of the present invention. In various embodiments, the biomaterials retain greater than 85%, 90%, 95%, 96%, 97%, 98%, 99% or 100% of the biological activity they exhibited prior to being patterned after being subjected to the methods of patterning of the instant invention.

This patterning process can be repeated to give multiple protein patterns on a single substrate. In an embodiment, following deposition of the first protein, another layer of fluorinated organic material is deposited and patterned by imprint lithography. A second layer of proteins is deposited and patterned. This process may be repeated multiple times as desired. In an embodiment, different types of biomaterials are deposited sequentially. In an embodiment, cells are deposited on the protein.

After deposition of the biomaterial, the patterned portion of organic material layer and attached biomaterial are selectively removed from the substrate by contacting the substrate with a fluorinated solvent. Such a process can be referred to as a lift-off process. The fluorinated organic solvent interacts with the patterned layer to remove it and the associated biomaterial from the substrate. It is desirable the fluorinated organic solvent have a fluorine content such that the fluorinated organic material is sufficiently soluble in the solvent to remove it from the substrate. Also, it is desirable that the fluorinated organic solvent not adversely affect the biological material (e.g., not have functional groups that compromise biomolecule functionality). In an embodiment, the fluorinated organic solvent is a hydrofluoroether.

Examples of suitable fluorinated organic solvents include, but are not limited to, hydrofluoroethers (HFEs) (e.g. $C_xH_y\text{-}OC_zF_w$) such as, methyl nonafluorobutyl ether, methyl nonafluoroisobutyl ether, isomeric mixtures of methyl nonafluorobutyl ether and methyl nonafluoroisobutyl ether, ethyl nonafluorobutyl ether, ethyl nonafluoroisobutyl ether, isomeric mixtures of ethyl nonafluorobutyl ether and ethyl nonafluoroisobutyl ether, 3-ethoxy-1,1,1,2,3,4,4,5,5,6,6,6-dodecafluoro-2-trifluoromethylhexane, 1,1,1,2,2,3,4,5,5,5-decafluoro-3-methoxy-4-trifluoromethyl-pentane, 1,1,1,2,3,3-hexafluoro-4-(1,1,2,3,3,3,-hexafluoropropoxy)-pentane and combinations thereof. HFEs are commercially available from, for example, 3M and Fluoryx. Other examples of fluorinated solvents include, but are not limited to, solvents such as perfluoroethers (e.g., $C_xF_yOC_zF_w$) and the like.

In an embodiment, the pattern is formed by imprint lithography and residual, fluorinated organic material (fluorinated organic material not part of the patterned portion of fluorinated organic material layer), if any, is removed from the substrate by contacting the substrate from step c) with an argon/oxygen plasma.

In another aspect, the present invention provides a pattern of biological material or a plurality of biomaterials on a substrate formed by the methods described herein. In an embodiment, the present invention provides a substrate with at least one surface having a pattern of biomaterials (e.g., a protein) thereon. In another embodiment, the present invention provides a substrate with at least one surface having a plurality of patterns of biomaterials (e.g., a protein(s)) thereon.

In yet another aspect, the present invention provides a device comprising a pattern of biological material or a plurality of biomaterials on a substrate formed by the methods described herein. Examples of such devices include, but are not limited to, biosensors, bio-MEMs, biomolecule arrays and microfluidic devices, and the like.

In an embodiment, the device is an organic electronic device. For example, the device can be lab-on-a-chip or protein chip device comprising an array of patterned protein(s).

EXAMPLE 1

This example describes the preparation and use of fluorinated polymers in the present invention.

Here, it is shown that these hydrofluoroether solvents, along with a fluorinated resist, are benign to biomolecules in that the solvents do not adversely affect the biomolecules and are capable of serving as a processing system for patterning biomolecules by lithography. By employing a benign set of processing conditions, proteins and DNA may be directly and universally patterned by this lithography technique. In this way, high-resolution and high-throughput biomolecule patterning can be accomplished with precise alignment capabilities through this repeatable lithographic process.

Imprint lithography was used to demonstrate the lithographic patterning properties of this biocompatible processing system. Imprint lithography has recently received significant attention as a patterning technique with the potential to assume a key role in the manufacture of nanoscale structures for electronic, optical, biological, and energy applications. Because of its ability to produce patterns as small as 10 nm over large areas, high-reproducibility, and high-throughput, imprint lithography has also found applications in protein patterning. One particular advantage of protein patterning by imprint lithography is that biomolecules are not exposed to the denaturing effects of UV radiation as found with photolithography. However, as with photolithography, imprint lithography also typically requires harsh resists and developers. Traditional harsh processing system were replaced with a biocompatible one and demonstrate lithographic patterning of both a two-protein and three-protein array. In addition, this resist and patterning technique were shown have the ability to pattern protein arrays suitable for cell surface response studies.

Materials

Benzotrifluoride (TFT) and 3,3,4,4,5,5,6,6,7,7,8,8,9,9,10,10,10-Heptadecafluorodecyl methacrylate were purchased from Sigma Aldrich (St. Louis, Mo.) and used as received. 2,2,3,3,4,4,5,5,6,6,7,7,8,8,9,9-Heptadecafluorononyl methacrylate was purchased from Synquest Labs, Inc. (Alachua, Fla.) and used as received. Azobisisobutyronitrile (AIBN) was purchased from Sigma Aldrich and recrystalized from $CHCl_3$. 3M™ Novec™ Engineered Fluid HFE-7200 and 7500 were purchased from 3M™ USA (St. Paul, Minn.).

Bovine serum albumin (BSA), Biotin-BSA (for US experiments), streptavidin labeled with horseradish peroxidase (streptavidin-HRP) and Rabbit γ Globulin (IgG) were purchased from Sigma Aldrich and used as received. Dinitrophenyl-BSA (DNP-BSA) was prepared from BSA conjugated to 2,4-dinitrophenyl (DNP), purchased from Invitrogen (Carlsbad, Calif.), with a yield of approximately 20 DNP per BSA. Cy3 and Cy5 fluorescent dyes were purchased from GE Healthcare Life Sciences (Piscataway, N.J.) and conjugated to DNP-BSA, with a yield of about four Cy3 and Cy5 dye molecules per DNP-BSA. Mouse monoclonal anti-DNP Immunoglobulin E (IgE) was purified according to a previously published procedure. The IgE was then modified with AlexaFluor 488 (A488), purchased from Invitrogen, according to the labeling kit instructions. Streptavidin-AlexaFluor 568 (streptavidin-A568), streptavidin-AlexaFluor 546 (streptavidin-A546), and goat anti-Rabbit IgG AlexaFluor 405 (anti-Rabbit A405) were purchased from Invitrogen and used as received. Goat anti-Rabbit IgG AlexaFluor 647 (Goat anti-Rabbit A647) was prepared from Goat anti-Rabbit IgG, purchased from Jackson ImmunoResearch Laboratories, Inc. (West Grove, Pa.), and conjugated to AlexaFluor 647 (A647), purchased from Invitrogen, with a yield of about nine A647 per anti-Rabbit IgG. The 20 mer DNA probe 5'-CTGAACG-GTAGCATCTTGGA-3' [SEQ ID NO: 1] construct with biotin at its 5'-terminus and the 20-mer target DNA 5'-TC-CAAGATGCTACCGTTCAG-3' [SEQ ID NO: 2] construct with A488 at its 5'-terminus were purchased from Integrated DNA Technologies (San Diego, Calif.) and used as received. Immunopure streptavidin and ABTS peroxidase substrate were purchased from Pierce (Rockford, Ill.). Mouse monoclonal antibodies (Mab clones AP003S and BP005S) against prostate specific antigen (PSA) were purchased by Scripps Laboratories (San Diego, Calif.). Free-PSA calibrators in human serum were obtained from CIS Bio-International (Bagnols-sur-Ceze, France). Biotin-BSA (for Greece experiments) and mouse monoclonal anti-PSA antibody (clone BP005S) were prepared according to a published method. MaxiSorp polystyrene 96 well-plates were from Nunc (Roskilde, Denmark).

Compounds were characterized by $^1H$ NMR, $^{13}C$ NMR, elemental analyses and mass spectrometry. Thermal properties were studied by thermo gravimetric analysis (TGA). Size exclusion chromatography was conducted in a fluorous solvent at Asahi Glass Japan.

Buffer Solutions.

Biotinylated BSA solution: 0.9 g of NaCl and 1 g BSA are added to 100 mL 0.05 M pH 6.5 phosphate buffer solution. 5 μg/mL biotinylated BSA was dissolved in the solution. Alexafluor-streptavidin solution: 0.9 g of NaCl and 1 g BSA are added to 100 mL 0.05 M pH 6.5 phosphate buffer solution (recipe above). 5 μg/mL streptavidin was dissolved in the solution. Protein stock solutions: stock solutions of proteins are prepared by dissolving 1 mg/mL of protein in the 0.05 M pH 9.2 carbonate buffer (recipe above). Protein solutions for deposition: 25 μL of each protein stock solution are added to each 1 mL of 0.05 M pH 6.5-7.0 phosphate buffer solution to prepare the final solution of proteins that are deposited on the substrates for adsorption and patterning.

Methods. Synthesis and Characterization of Imprint Resist 1 (5-1).

To a 25 cm³ Schlenk tube. 7.00 g (13.15 mmol) of 3,3,4,4,5,5,6,6,7,7,8,8,9,9,10,10,10-Heptadecafluorodecyl methacrylate was added followed by 0.07 g (0.43 mmol) AIBN and 7 cm³ benzotrifluoride. The tube was then sealed and degassed by three freeze-thaw cycles in liquid $N_2$ under reduced pressure. The reaction was stirred at 75° C. for 12 hours under a $N_2$ atmosphere. The solution was then precipitated in hexanes and dried under reduced pressure to give a colorless solid 2 (FIG. 1), yielding 6.5 g (93%). Analysis of Imprint Resist 1: IR: ν=1732, 1194, 114, 704, 655, 559 cm⁻¹; $^1H$ NMR (400 MHz, $CDCl_3$:$CFCl_3$ (v/v)): δ=4.25 (br s, 2H, $CH_2CF_2$), 2.49 (m, 2H, $CH_2CH_2CF_2$), 1.67-0.80 ppm (m, 5H); $T_d$ (TGA)=168.92° C.; $M_n$=611,000; $M_w/M_n$=1.2.

Synthesis and Characterization of Imprint Resist 2 (5-2).

2,2,3,3,4,4,5,5,6,6,7,7,8,8,9,9-heptadecafluorononyl methacrylate (7.00 g, mmol) was added to a 25 cm³ Schlenk tube. Benzotrifluoride (7 cm³) and AIBN (0.07 g, 0.43 mmol) were then added to the mixture. The tube was sealed then degassed by three freeze-thaw cycles in liquid $N_2$ under reduced pressure. The solution was magnetically stirred at 75° C. for 12 hours under a $N_2$ atmosphere. The solution was precipitated in hexanes then dried under reduced pressure to give a colorless solid (5.91 g) in approximately 84% yield. Analysis of Imprint Resist 2. IR: ν=1734, 1199, 1142, 704, 655, 555 cm⁻¹; $^1H$ NMR (400 MHz, $CDCl_3$ (1 part by volume)+CFCl$_3$ (1 part by volume), δ): =4.23 (br s, 2H, CH$_2$CF$_2$), 2.47-0.78 ppm (m, 5H); T$_d$ (TGA)=165.55° C.

Lithographic Evaluation.

The lithographic properties of the Imprint Resist 1, using two different substrates of silicon and optical glass wafers, were investigated using a Nanonex NX-2500 nanoimprint lithography tool. The resist films were spin-coated from a solution of polymer (0.15 g) in hydrofluoroether 7500 (HFE 7500, 1.5 g) at 1000 rpm followed by post-apply bake (PAB) at 40° C. The resulting films had a thickness of ca. 600 nm. Films were imprinted at 300 psi and 50° C. for 5 minutes with a fused silica stencil with ca. 600 nm feature relief. The imprint stencil was prepared through standard photolithographic technique on a fused silica mask with feature sizes 1 μm to 100 μm. After imprint, the film was Ar/O$_2$ plasma etched on an Oxford PlasmaLab 80+ ME System.

Protein-Moiety Interaction Compatibility Assay:

The effect of Imprint Resist 1 and hydrofluoroether solvents on streptavidin-biotin interactions was investigated. Streptavidin solutions of final concentrations 1 μg/mL, 2 μg/mL, and 5 μg/mL were prepared in carbonate buffer containing 43 mM NaHCO$_3$, 7 mM Na$_2$CO$_3$, and 0.05% NaN$_3$ (pH 9.2). 100 μl solutions were deposited into three separate sets of microtitration wells and left for 1 hour at room temperature (RT) to adsorb, decanted, and then washed twice with a no-salt washing buffer containing 400 μM Tris-HCl (pH 8.25). Nonspecific binding was then blocked with addition of a concentrated BSA solution containing 100 mM NaHCO$_3$ supplemented with 10 mg/mL BSA, which was left for 1 hour at RT to adsorb. Wells were washed as previously described and followed by two washings with distilled water.

To one set of wells (Set 1), including each of the 1 μg/mL, 2 μg/mL, and 5 μg/mL streptavidin concentrations, no-salt washing buffer solution was added. To a second set of wells (Set 2), hydrofluoroether solvent was added. To the third set of wells (Set 3), a 10% (w/v) solution of Imprint Resist 1 dissolved in FIFE 7500 was added and left in the wells for 2 minutes at RT and then decanted. Set 3 wells were then baked for 5 minutes at 50° C. To remove the resist, Set 3 wells were washed in hydrofluoroether solvent four times for 3 minutes each while shaking, which mimics the processing conditions of lithographic patterning. The wells of Sets 1 and 2 remained filled with buffer and solvent, respectively, for the whole duration of Set 3's processing. All wells in Sets 1, 2, and 3 were finally decanted and washed with both distilled water and no-salt washing buffer solution (pH 8.25).

To test for the binding capacity of the immobilized streptavidin, 100 μl phosphate buffer solution (PBS, 16 mM Na$_2$HPO$_4$-2H$_2$O, 34 mM KH$_2$PO$_4$, pH 7.0) containing either 10 mg/mL BSA (blank) or 100 ng/mL biotinylated BSA were added to the wells and incubated for 30 minutes at RT. Following streptavidin-biotin binding, wells were rinsed four times with TWEEN washing buffer containing 400 μM Tris-HCl, 15 mM NaCl, and 0.05% TWEEN20 (v/v). In order to detect the bound biotin, a solution of 250 ng/mL streptavidin-HRP in PBS (pH 7.0) containing 10 mg/mL BSA was deposited in all wells and incubated for 15 minutes at RT while shaking. Wells were washed as previously described. The presence of streptavidin-HRP was determined via addition of ABTS peroxidase substrate solution and incubation for 30 minutes at RT while shaking. Absorption signals were measured at 405 nm on a Labsystems Multiskan RC microplate reader.

Antibody-Antigen Interaction Compatibility Assay.

The effect of Imprint Resist 1 and hydrofluoroether solvents on monoclonal antibody-antigen binding was investigated. A 100 μl solution of 5 μg/mL mouse monoclonal antibody-prostate specific antigen (Mab-PSA) in carbonate buffer (pH 9.2) was deposited into three separate sets of microtitration wells and incubated overnight at RT to adsorb. Wells were then washed, blocked, separated into three sets, and processed as described previously for the protein-moiety binding assay.

The binding capacity of the immobilized antibody was investigated by testing for free-PSA using the three different sets of wells. To each set of wells, free-PSA calibrator solutions (0, 0.39, 0.95, 2.48, and 4.9 ng/mL) and 5 μg/mL biotinylated anti-PSA antibody solution in 50 mM Tris-HCl buffer (pH 8.25, 15 mM NaCl, 5 mg/mL BSA) were added and incubated for 1 hour at RT while shaking. Wells were then washed four times with TWEEN washing buffer. Following this, free-PSA was detected via addition of streptavidin-HRP and ABTS peroxidase substrate solution as described previously for the protein-moiety binding assay. Absorption signals were once again measured at 405 nm on a Labsystems Multiskan RC microplate reader.

DNA Complementary Strand Compatibility Assay:

The effect of Imprint Resist 1 and hydrofluoroether solvents on the binding of complementary DNA strands was investigated. A 20-mer probe 5'-CTGAACGGTAGCATCT-TGGA-3' was selected because of its previously reported ability to stably complex with its complementary target sequence 5'-CCAAGATGCTACCGTTCAG-3' at RT. The DNA probe was end-labeled with biotin at its 5'-terminus. For fluorescence detection, the target DNA was end-labeled with A488 at its 5'-terminus.

Silicon wafers were patterned with 1 μm to 5 μm features using the parylene lift-off method as previously described. These wafer chips were first patterned with a protein monolayer containing streptavidin-A568 (25 μg/mL in PBS, pH 7.0) for 30-60 minutes at RT and followed by rinsing with PBS (pH 7.0). Nonspecific binding was blocked by incubation with 1 mg/mL BSA in PBS (pH 7.0) for 15 minutes at RT and followed by rinsing again with PBS (pH 7.0). To assemble the ssDNA monolayer, wafer chips were incubated with 1 μM biotinylated DNA probe in PBS for 30-45 minutes at RT, followed by rinsing three times with PBS (pH 7.0). Wafer chips were then incubated with a solution of PBS (pH 7.0), hydrofluoroether solvents, or Imprint Resist 1 for 5 minutes at RT. In the event of resist application, the resist was baked for 5 minutes at 37° C. and removed via three separate washes with HFE 7200. To detect for the binding of complementary DNA strands, all wafer chips were then rinsed three times with PBS (pH 7.0) and exposed to 0.75 μM A488-labeled target DNA in PBS for 30 minutes at 37° C. followed by 15 minutes at RT. Wafer chips were then quenched with 1 mg/mL BSA in PBS (pH 7.0) and the parylene coat was removed. DNA patterned arrays were imaged using a ×63 (NA of 1.4) oil immersion objective lens on a Zeiss 710 confocal microscope. A488-target DNA was excited using the 488 nm line of an argon laser. Streptavidin-A568 was excited using a 561 nm laser line. Acquired images were processed with ImageJ software.

Protein Stability Over Repeated Cycles of Imprint Lithography Assay.

The stability of previously patterned proteins undergoing multiple cycles of resist application and removal was investigated using Imprint Resist 1 and hydrofluoroether solvents.

Silicon wafers were first hydrophylized for 20 minutes in Piranha solution (1:1 v/v concentrated $H_2SO_4/30\%$ $H_2O_2$) and then thoroughly washed with distilled water. After drying the wafers under a stream of nitrogen, they were immersed in 2% (v/v) aqueous APTES solution for 20 minutes at RT. Wafers were gently washed, dried with nitrogen, and baked for 20 minutes at 120° C. Then, one wafer was coated with a 25 µg/mL of a biotinylated-BSA solution in PBS (pH 7.0) for 1 hour at RT, while a second wafer was coated with 25 µg/mL BSA solution for blank measurements. Both wafers were washed with PBS (pH 7.0) and blocked with a 10 mg/mL BSA solution in the same buffer for 1 hour at RT. After rinsing with washing solution (400 µM Tris-HCl, 15 mM NaCl, pH 8.25) and distilled water, the wafers were then dried and a piece of each was cleaved off to be kept as a control. The remaining wafers were spin-coated with Imprint Resist 1, baked for 5 minutes at 50° C., and developed with hydrofluoroether solvent to remove the resist.

The resist application/removal cycle was repeated up to ten times. A piece was cut from each wafer after 1, 2, 4, 6, 8, and 10 cycles. All wafer pieces were then covered with a 5 µg/mL streptavidin-A546 in PBS (pH 7.0) containing 10 mg/mL BSA, and incubated for 30 hours at RT. After washing with PBS (pH 7.0) containing 0.05% (v/v) TWEEN20 and distilled water, the chips were dried with nitrogen gas. The stability of the protein adsorption to repeated resist application/removal cycles was evaluated by fluorescence intensity measurements on images (5 each) acquired via an Axioscope 2 Plus epifluorescence microscope facilitated with a Sony Cyber-Shot digital camera and processed with the ImagePro Plus software.

Multiple-Cycles Tests.

The repeatability of this patterning method was investigated by testing the effect of multiple applications and removals of the imprint resist 5-1 in hydrofluoroether solvents on biotin-BSA. An assay, similar to the BSA assay described in Section 2.5.1 of this chapter, was performed on an aminosilanized silicon substrate coated with biotinylated BSA: Imprint resist 5-1, 10 wt. % solution in hydrofluoroether solvent, was deposited onto the surface and left for 2 minutes at ambient temperature. The sample was baked for 5 minutes at 50° C. and then the resist was removed by washing with hydrofluoroether solvents. This resist deposition and removal step was repeated ten times to mimic the lithographic processing steps required to create a ten-protein array. Biomolecule functionality was measured by fluorescence intensity for 0, 2, 4, 6, 8, and 10 resist deposition and removal cycles.

Fabrication of Protein Arrays.

Patterned arrays containing one, two, and/or three different proteins were fabricated via the following technique. Imprint Resist 1 was spun-cast from solution in HFE 7500 onto a silicon substrate to yield a ca. 600 nm polymer film. The film was imprinted and $Ar/O_2$ plasma etched as described previously. A layer of APTMS was then vapor deposited using an Applied Microstructures MVD100 vapor deposition tool. Protein solutions containing 25 µg/mL of each individual protein in PBS (pH 7.0) were prepared. These protein solutions included DNP-BSA, biotin-BSA, and Rabbit IgG. The first protein solution was allowed to incubate for 1 h at RT on the wafer surface before being rinsed with additional PBS (pH 7.0). Following the deposition of the first protein, the resist was removed using washes with hydrofluoroether solvent while shaking. Onto the first patterned protein layer, another layer of polymer resist was spun-coat and patterns were then imprinted and etched offset from the initial protein layer. APTMS was once again vapor deposited on the surface of the resist. A second protein solution was incubated for 1 hour at RT on the wafer surface before being rinsed with PBS (pH 7.0) and having the resist removed with hydrofluoroether solvent. This entire process was repeated again for addition of a third protein in those cases when a three-protein patterned array was desired.

Post multi-protein immobilization, photoresist was removed using 10 minutes washes with hydrofluoroether solvent while shaking. To prevent nonspecific binding of fluorophores, wafer chips were incubated with 10 mg/mL BSA in PBS (pH 7.0) for 15 minutes at RT followed by rinses with PBS. For detection of each protein, corresponding fluorophore solutions (25 µg/mL in PBS, pH 7.0) were added in separate incubations atop the wafer chips for 30-45 minutes each at RT followed by rinsing with distilled water between each fluorophore addition. Biotin-BSA was detected using Streptavidin-A568; DNP-BSA using A488-IgE; and rabbit IgG using goat anti-rabbit A405 and/or goat anti-rabbit A647 respectively. Fluorescence microscopy was performed using an Olympus BX51 upright microscope with an LMPlanFI 20× dry objective lens (N.A. 0.40). Images were acquired with a Roper CoolSnap HQ CCD camera and Image Pro software. Goat anti-rabbit IgG-A405 was observed with a 360 nm excitation/460 nm emission filter set; A488-IgE with a 470 nm excitation/525 nm emission filter set; Streptavidin-A568 with a 545 nm excitation/605 nm emission filter set; and goat anti-rabbit IgG-A647 with a 620 nm excitation/700 nm emission filter set. Acquired images were processed with Igor Pro 6.11 software.

Cell Culture.

Rat basophilic leukemia (RBL-2H3) cells were maintained in a monolayer culture in Minimum Essential Medium (MEM) from Invitrogen supplemented with 20% Fetal bovine serum (FBS), purchased from Atlanta Biologicals (Lawrenceville, Ga.), and 10 µg/mL gentamicin sulfate, purchased from Invitrogen. Cells were harvested with trypsin-ethylenediaminetetraacetic acid (trypsin-EDTA, purchased from Invitrogen) three to five days after passage.

Protein-Assisted Cell Patterning.

A silicon substrate was lithographically patterned with Imprint Resist 1. Onto this surface, DNP-BSA, conjugated to a cyanine fluorescent dye (Cy3-Cy5), was deposited and left for 1 hour at RT to adsorb. The resist was removed, using washes in hydrofluoroether solvent, leaving the patterned DNP-BSA Cy3-Cy5 behind. RBL-2H3 cells were sensitized by incubating for 40-60 minutes at 37° C. with 2-3 µg/mL A488-IgE, specific for DNP. Cells, suspended at a concentration of $1-2 \times 10^6$ cells per mL, were added to the protein patterned substrate (8×8 mm) in the center of a 35-mm Petri dish with coverglass bottom (0.16-0.19 mm; MatTek Corp., Ashland, Mass.), as described by Torres et al. After 30-60 minutes of incubation at 37° C., cells were fixed with 4% paraformaldehyde in PBS for 20 minutes followed by quenching with 10 mg/mL BSA in PBS (pH 7.0). Post fixation, cell-protein patterned substrates were imaged using a ×63 (NA of 1.4) oil immersion objective lens on a Zeiss 710 confocal microscope. A488-IgE was excited using the 488 nm line of an argon laser and Cy3-Cy5 DNP-BSA using a 561 nm laser line. Acquired images were processed with ImageJ software.

Results

Imprint Resist 1 is Patternable.

Imprint Resist 1 was synthesized by radical polymerization with AIBN as the radical initiator (FIG. 1). The resist structure was designed to be fluorinated enough to be processable in hydrofluoroether solvents and also free of unnecessary functional groups that might interact with biomolecules. The resulting polymer demonstrated sufficient solubility to be processable in hydrofluoroether solvents HFE 7200 and HFE 7500. The compatibility of the resist with biomolecules is investigated further in the proceeding results.

Figure 2:
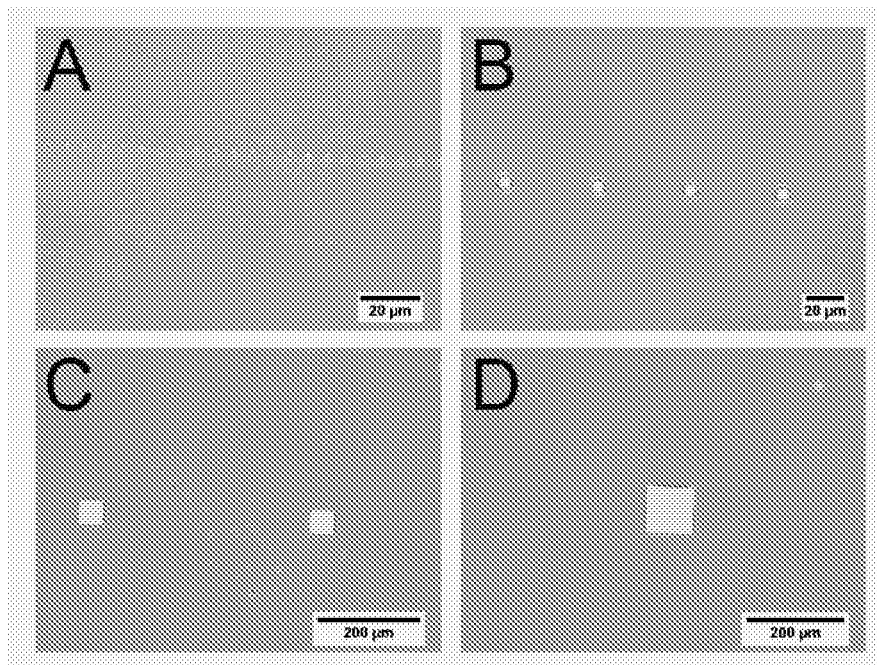
FIG. 2. Imprint Resist 1 patterned by imprint lithography: (a) 1 μm features, (b) 5 μm features, (c) 50 μm features, and (d) 100 μm features.

To demonstrate patterning properties, Imprint Resist 1 was tested using imprint lithography. During imprint lithography, a pattern is "stamped" into the resist via heat and pressure, rather than relying on UV-exposure techniques required by traditional photolithography, which cause biomolecule damage and degradation. Films of Imprint Resist 1 were spun-cast from solution in HFE 7500 onto a wafer surface. Imprinting was carried out at 50° C. and 300 psi. The 50° C. temperature was found to be high enough to support patterns, yet low enough to avoid major protein degradation (data not shown). Square features ranging in size from 1 µm to 100 µm were obtained using a silica template with 1 µm to 100 µm features, ca. 600 nm relief, and subsequent $Ar/O_2$ plasma etching. Patterned Imprint Resist 1 is shown in FIG. 2.

Extensive testing was performed to ensure that neither HFEs nor the fluorinated resist had any adverse effects on the biomolecules. Functionality of representative proteins was tested following extended exposure to HFEs and fluorinated resist, which showed that the proteins were uneffected by neither the HFEs nor resist.

Imprint Resist 1 is Compatible with Streptavidin-Biotin Interactions.

Figure 3:
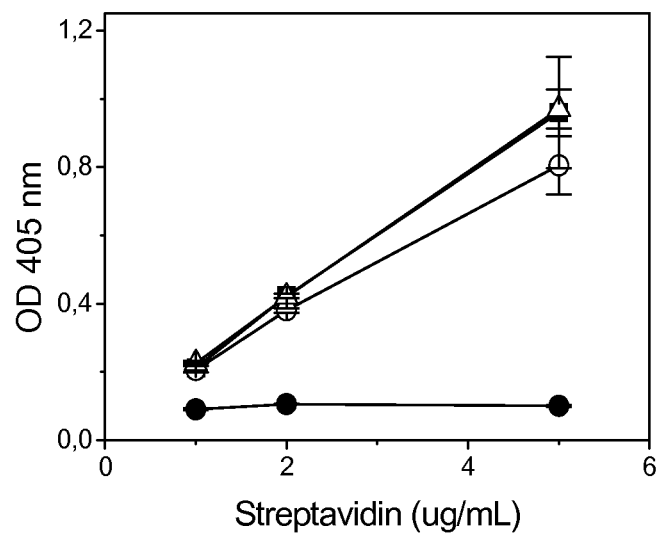
FIG. 3. Effect of hydrofluoroether solvent and resist application/removal onto immobilized streptavidin's binding capacity. Wells coated with streptavidin were incubated with washing solution (control set; closed squares), with hydrofluoroether solvent (open circles), or were subjected to resist application/removal (open triangles). There were then tested by applying a sandwich type assay for biotinylated-BSA as described in the Methods section. A line corresponding to blank values obtained using control wells not reacted with biotinylated-BSA is also provided (closed circles). Each data point corresponds to the mean absorbance values of four measurements; error bars correspond to ±SD.

The compatibility of Imprint Resist 1 with patterning protein-moiety interactions was investigated. A streptavidin-biotin assay was performed to determine the effect of the polymer resist and hydrofluoroether solvents on binding between the protein and moiety. For the assay, resist and hydrofluoroether solvents were deposited onto adsorbed streptavidin proteins so as to mimic the lithographic processing steps required for patterning. The ability of streptavidin to bind biotin-BSA following exposure to resist and hydrofluoroether solvents was tested and compared to a control set which received only buffer, as shown in FIG. 3. To detect the presence of biotin in each well, a second avidin-containing protein was added in the form of streptavidin-HRP. In the presence of ABTS peroxidase substrate, the HRP enzyme modifies the substrate to produce a measurable fluorescent signal. Fluorescence absorption signals were measured and compared to the control sample set.

As shown in FIG. 3, the immobilized streptavidin was not affected by the resist application/removal procedure. At each streptavidin concentration, the optical density (OD) values for those samples treated by resist application/removal are within standard deviation of those control samples treated only with washing buffer. However, it should be noted that samples treated solely with hydrofluoroether solvents (open circles) did produce a slight decrease (5-18%) in the binding capacity of immobilized streptavidin. Control wells (blanks) not reacted with biotin-BSA, but washed with buffer are shown as closed circles. In addition, separate controls for treatment with the solvent and/or resist were performed in the absence of biotin-BSA. These results were not statistically different from the blank values shown.

Figure 11:
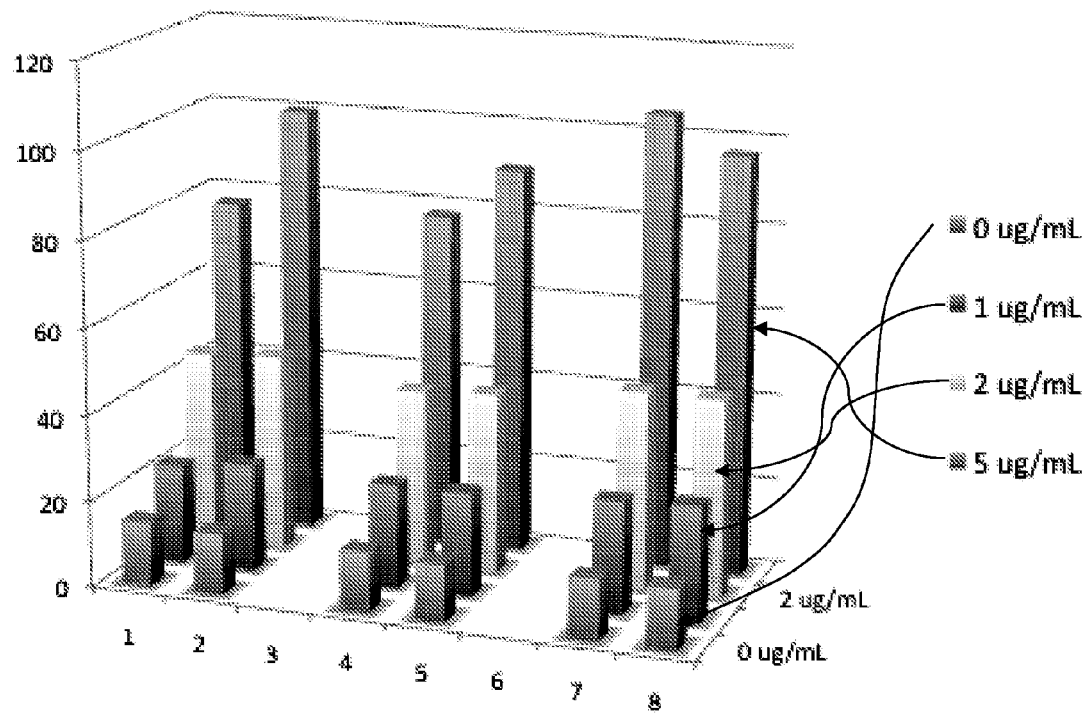
FIG. 11. Results of BSA/resist biocompatibility assay. Two sets of data were taken for each condition. The graph shows the increasing concentrations of streptavidin used in the assay, from 0 μg/mL to 1 μg/mL, 2 μg/mL, and 5 μg/mL along the Y-axis. The Z-axis gives normalized percentages of the absorption signals, using the highest experimental control-set absorption signal as 100%. Along the X-axis, from the left is the control set (1 and 2 on the X-axis). The middle set (4 and 5) shows the effect of hydrofluoroether exposure, and the rightmost data set (7 and 8) shows the effects of resist and hydrofluoroether solvent exposure.
Figure 12:
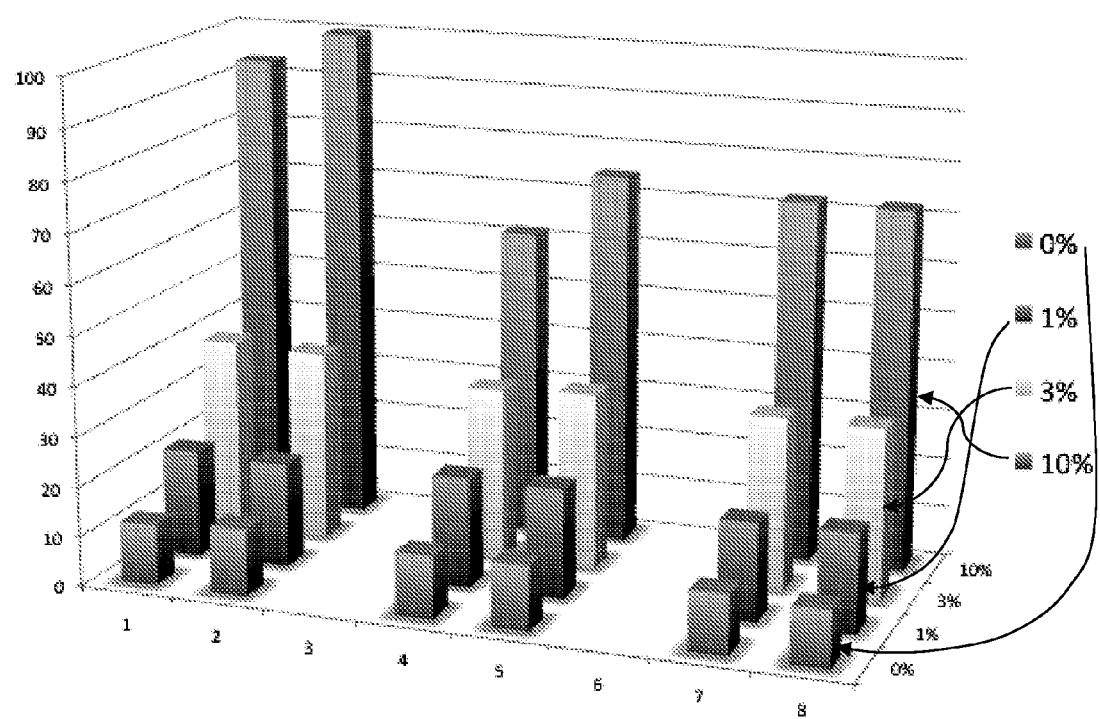
FIG. 12. Results of monoclonal antibody/resist biocompatibility assay. Two sets of data were taken for each condition. The graph shows the increasing percentages of PSA standard used in the assay, from 0% to 1%, 3%, and 10% along the Y-axis. The Z-axis gives normalized percentages of the absorption signals, using the highest experimental control-set absorption signal as 100%. Along the X-axis, from the left is the control set (1 and 2 on the X-axis). The middle set (4 and 5) shows the effect of hydrofluoroether exposure, and the rightmost data set (7 and 8) shows the effects of resist and hydrofluoroether solvent exposure.

The BSA assay demonstrates essentially no deterioration of biomolecule functionality, as the fluorescence intensity measurements are very similar to those of the control sets, which had no resist or hydrofluoroether exposure. In fact, the signals obtained for the control set are slightly lower than those obtained for the hydrofluoroether/resist exposure experimental set. These results suggest that both hydrofluoroether solvents and the imprint resist do not significantly affect the ability of streptavidin to bind to biotin. In the monoclonal antibody assay, the fluorescence signals for 1% and 3% are extremely similar. The signals at the higher concentration, 10%, show more variability; the experimental sets show lower absorption. This could be due to either partial denaturation of the antibodies or else experimental error of the assay itself. The absorption signals obtained for the BSA and monoclonal antibody assays are shown in FIGS. 11 and 12, respectively.

Imprint Resist 1 is Compatible with PSA Antigen-Antibody Interactions.

Figure 4:
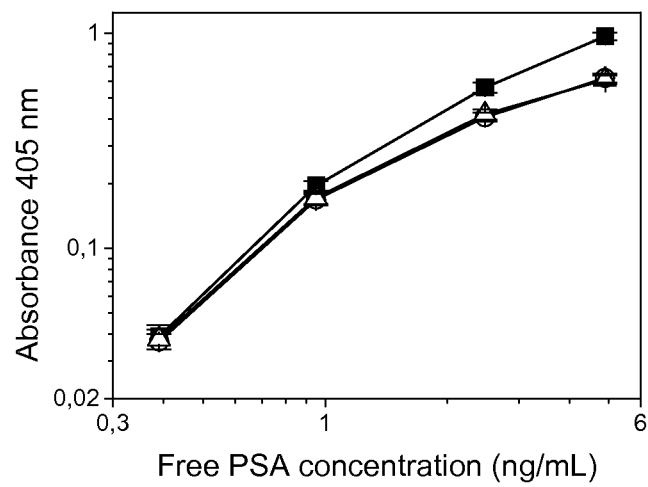
FIG. 4. Effect of hydrofluoroether solvent and resist application/removal onto immobilized monoclonal anti-PSA antibody's binding capacity. Wells coated with anti-PSA antibody were incubated with washing solution (closed squares), with hydrofluoroether solvent (open circles), or were subjected to resist application/removal (open triangles). They were then tested by applying a sandwich type assay to detect free-PSA as described in the Methods section. Each point corresponds to the mean absorbance values of three measurements; error bars correspond to ±SD. Control (blank) signal values have been subtracted in all cases.

The compatibility of PSA monoclonal antibody binding to PSA following exposure to hydrofluoroether solvents and Imprint Resist 1 was investigated. Similar to the protein-moiety assay described previously, hydrofluoroether solvents and resist were placed onto immobilized mouse monoclonal anti-PSA antibody under conditions which mimic lithographic processing conditions. Following this, a sandwich type assay involving the addition of both PSA standards and biotinylated anti-PSA antibody was performed. The presence of biotinylated anti-PSA antibody was then determined using addition of streptavidin-HRP and interaction with ABTS peroxidase substrate, as described previously for the protein-moiety assay. Fluorescence absorption signals were measured and thus represent only the free-PSA found in each well and not the total PSA present. These results were compared with the control samples, which did not receive solvent and/or resist applications (FIG. 4).

At low PSA standard concentrations (<1 ng/mL), the absorbance values for the control, solvent treated, and resist treated samples are similar. However, at higher PSA standard concentrations (2.48 and 4.9 ng/mL), both the solvent and resist treated samples showed a similar slight, yet significant, decrease in absorbance values as compared to the controls. Control well (blank) signal values have been subtracted in all cases.

Imprint Resist 1 is Compatible with Binding Complementary DNA.

The compatibility of Imprint Resist 1 with the binding of complementary strands of DNA was investigated. A DNA complementarity assay was performed to determine the effects of Imprint Resist 1 and hydrofluoroether solvents on patterned single-stranded DNA. A 20-mer DNA probe and its complementary target sequence were selected for this assay because of their ability to stably anneal at RT. Additionally, the DNA probe was synthesized with biotin at the 5'-terminus to serve as a linker. For fluorescence detection, the target complementary DNA strand was labeled with A488 at the 5'-terminus.

Square patterned arrays, formed using the parylene lift-off patterning method, were chosen to pattern the initial streptavidin protein layer. To ensure uniform adsorption of the protein to the silicon wafer surface, the streptavidin was conjugated to A568 for visualization. The DNA probe containing biotin was non-covalently bound to the initial streptavidin-A568. Samples then underwent treatment with control buffer, hydrofluoroether solvent, or resist application/removal so as to mimic lithographic processing techniques. The complementary ssDNA target-A488 was added to the biotin-DNA probe by first relaxing the DNA strands at 37° C. and then allowing them to anneal at RT.

Figure 5:
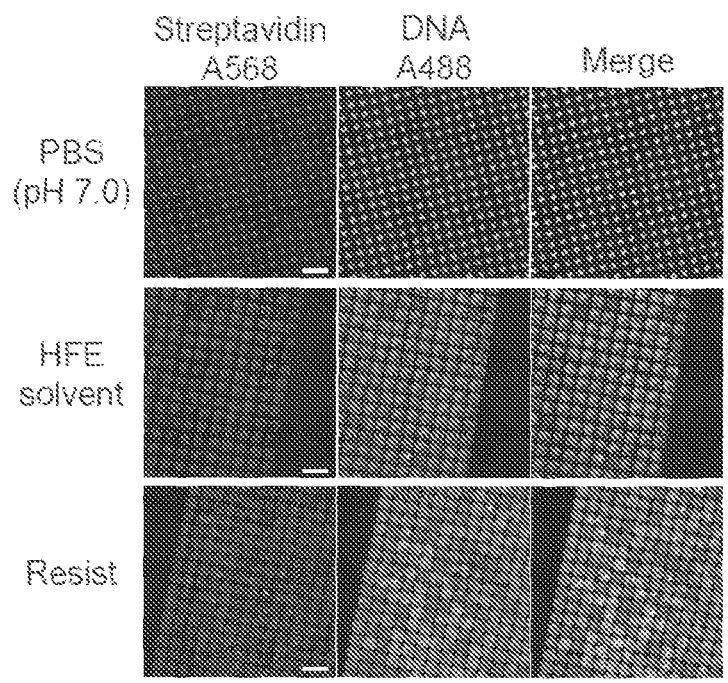
FIG. 5. Effect of hydrofluoroether solvent and resist application/removal on the binding of complementary strands of DNA. A biotinylated probe DNA was immobilized onto the wafer surface by binding to adsorbed streptavidin-A568. The surfaces were then treated with control buffer (PBS, pH 7.0), with hydrofluoroether solvent, or imprint resist application and removal. To determine stability of the probe DNA, a complementary target DNA-A488 strand was then added and detected using fluorescence microscopy. Scale bars represent 10 μm.
Figure 10:
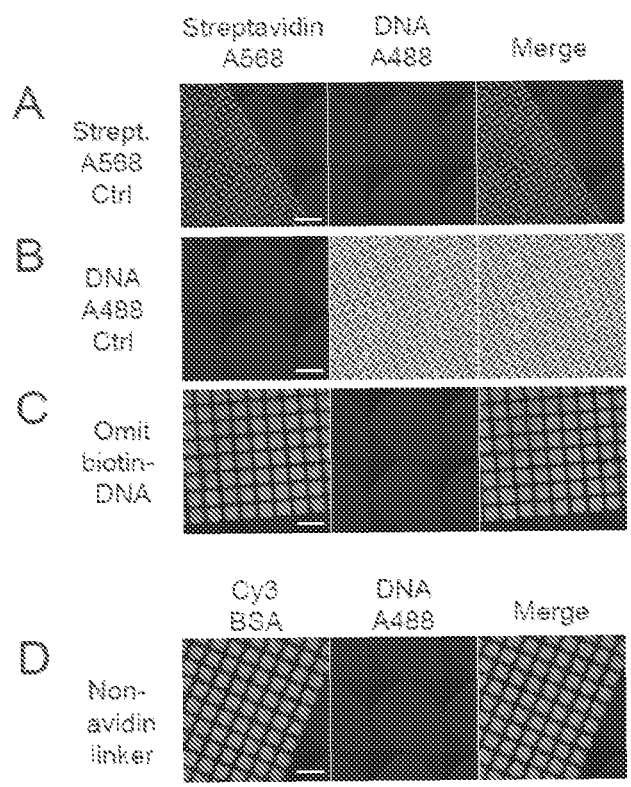
FIG. 10. Control tests for the effect of hydrofluoroether solvent and resist application/removal on the binding of complementary strands of DNA. In the original assay listed in the Methods section, biotinylated probe DNA was immobilized onto the wafer surface by binding to adsorbed streptavidin-A568. To determine stability of the probe DNA, a complementary target DNA-A488 strand was then added and detected using fluorescence microscopy. For control tests, conditions were changed from the original assay as follows: (A) adsorbed streptavidin-A568 only on a patterned surface, (B) target DNA-A488 bound to a non-fluorescently labeled avidin protein and probe biotin-DNA, (C) omission of probe biotin-DNA, and (D) use of a non-avidin protein linker as the initial layer adsorbed onto the patterned surface. Scale bars represent 10 μm.

Neither treatment with hydrofluoroether solvent nor resist deterred the ability of the target DNA-A488 strand to bind to the complementary DNA probe (FIG. 5). Additional controls were performed wherein the streptavidin or DNA probe strand were omitted to ensure the specificity of the binding between protein and DNA and/or the DNA strands (FIG. 10). Cy3-BSA protein was adsorbed to the wafer surface in place of streptavidin-A568 and both DNA strand solutions were applied as described in the Methods section. With no avidin protein available, the biotin-DNA probe was unable to bind to the surface, leaving the complementary target DNA-A488 unable to bind as well (FIG. 10D). Similarly, omission of the biotin-DNA probe left the complementary target DNA-A488 strand unable to bind to the adsorbed streptavidin proteins (FIG. 10C).

Multi-Layer Patterning does not Adversely Affect Previously Deposited Proteins.

Figure 6:
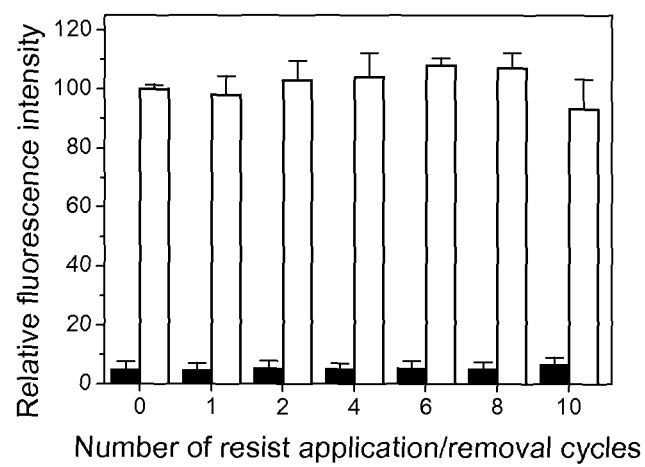
FIG. 6. Fluorescence intensity values obtained from aminosilanized Si surfaces coated with BSA (black columns) or biotinylated-BSA (white columns) and subjected to repeated resist application and removal cycles before being reacted with streptavidin-A546. The fluorescence values are expressed as percentages of the control sample value at 0 cycles. Each value is the mean of five measurements ±SD.

Further tests were performed to determine the potential of using Imprint Resist 1 and imprint lithography for multi-layer biomolecule patterning. Biotin-BSA solution was adsorbed onto a clean, aminosilanized silicon wafer surface. Imprint Resist 1 was then applied and removed with hydrofluoroether solvents multiple times to mimic lithographic patterning techniques. A small piece was cut off from the wafer at 0, 1, 2, 4, 6, 8, and 10 cycles of resist addition and removal. These ten cycles serve to imitate the processing effects of imprinting ten subsequent layers onto the first layer of biomolecule deposited. The chips were then incubated with streptavidin-A546 for detection of the protein remaining on the chip surface. The stability of protein adsorption after repeated resist application and removal cycles was evaluated by fluorescence intensity measurements. As shown in FIG. 6, the relative fluorescence intensity of streptavidin-A546 bound to biotin-BSA did not vary significantly over the course of ten resist application and removal cycles. A control series involving the adsorption of BSA (blank) solution was also performed and tested in parallel with the biotin-BSA wafer chips. Similar to the biotin-BSA results, the control BSA chips show no significant changes in fluorescence intensity over the course of the experiment.

Imprint Resist 1 can be Used for Orthogonal Patterning of Multiple Proteins.

Figure 7:
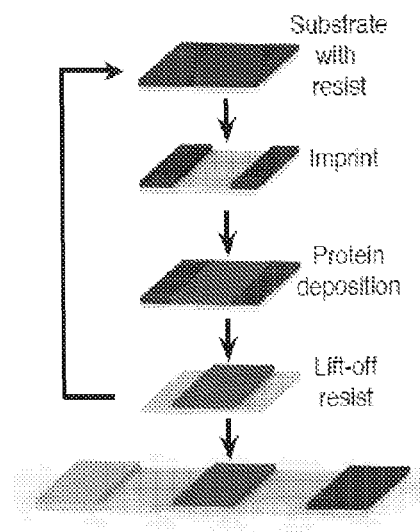
FIG. 7. Schematic for patterning a three-protein array by imprint lithography using Imprint Resist 1 and hydrofluoroether solvent.

To demonstrate the potential of Imprint Resist 1 and imprint lithography for multicomponent biomolecule patterning, protein arrays containing one, two, and three different proteins were fabricated. Clean silicon wafers coated with Imprint Resist 1 were patterned using the imprint lithography technique described in the Methods section. Following etching and aminosilanization of the patterned surface, the first protein solution was allowed to adsorb across the entire patterned area (FIG. 7). Washing with hydrofluoroether solvent allowed for removal of the resist while retaining the adsorbed patterned protein. For multi-protein patterning, a new layer of Imprint Resist 1 was applied to coat the entire wafer. New patterns were imprinted, etched, and aminosilanized offset by 50-100 μm from the first protein patterned underneath. After protein deposition, the resist was removed. The resist was reapplied and patterned again in those instances when a three-protein array was desired.

Figure 8:
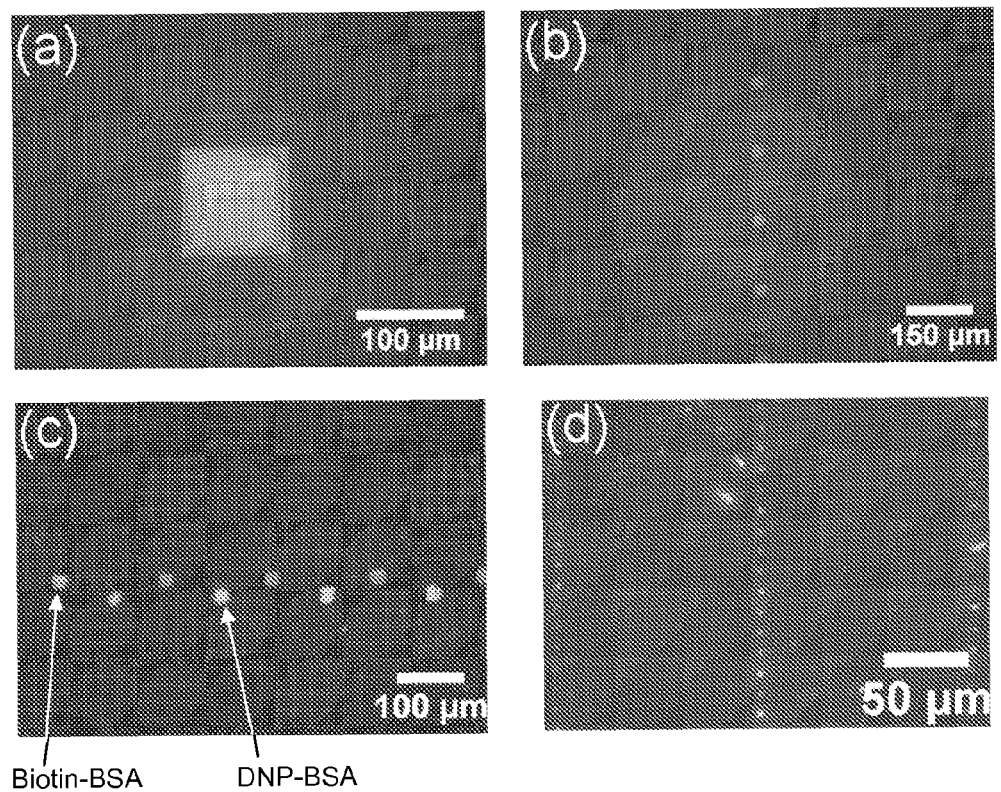
FIG. 8. Fluorescence microscopy images of single and multi-protein patterns prepared using Imprint Resist 1 and hydrofluoroether solvent. (a) 100 μm square of patterned DNP-BSA on silicon, (b) 20 μm squares of patterned DNP-BSA on silicon, (c) 20 μm squares of patterned DNP-BSA (examples indicated by arrows) and Biotin-BSA (examples indicated by arrows), (d) 1 μm squares of patterned DNP-BSA, biotin-BSA and rabbit γ globulins.

To demonstrate multi-protein patterning with Imprint Resist 1 and hydrofluoroether solvent, DNP-BSA, biotin-BSA, and rabbit IgG proteins were patterned in subsequent layers onto silicon wafer surfaces with feature sizes ranging from 1 μm to 100 μm. Following protein deposition, separate solutions of fluorescently labeled IgE, streptavidin, and anti-rabbit antibody were added to specifically label their corresponding proteins. Patterns were then imaged with fluorescence microscopy. Images of single protein patterns, a two-protein array, and a three-protein array are depicted in FIG. 8.

A small amount of residual resist remained on the three-protein array following resist removal, which was nonspecifically labeled by the fluorophores, especially A405 (FIG. 8D).

Imprint Resist 1 is Compatible with Protein-Assisted Cell Patterning.

Figure 9:
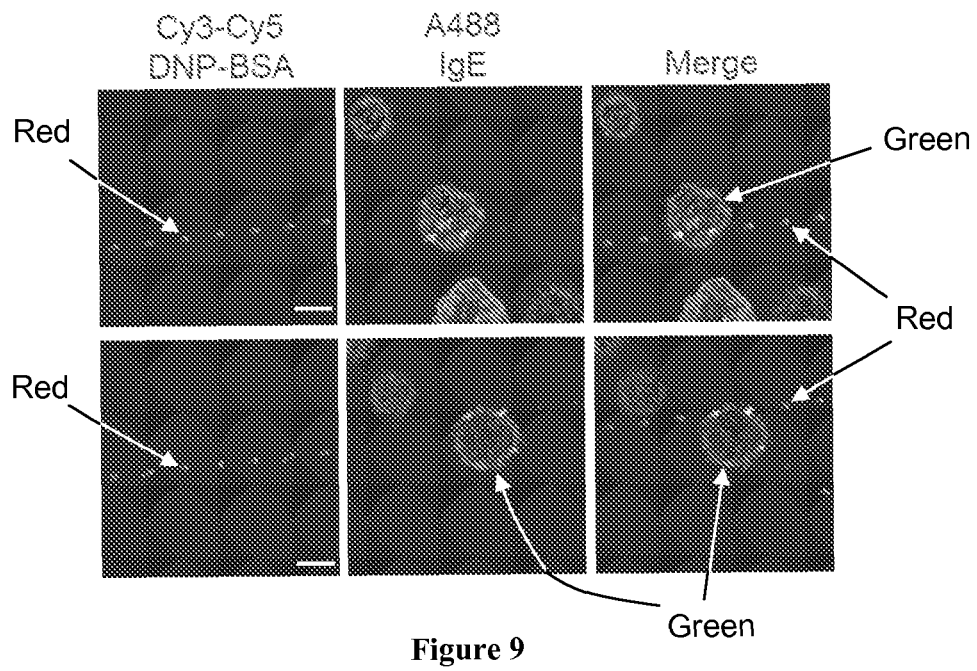
FIG. 9. Fluorescence microscopy images of RBL-2H3 cells sensitized with A488-IgE (green, examples indicated by arrows) and stimulated by Cy3-Cy5 DNP-BSA (red, examples indicated by arrows) patterned proteins. Proteins were patterned using Imprint Resist 1 and imprint lithography techniques. Scale bars represent 10 μm.

Further tests were performed to demonstrate the capabilities of this resist and patterning method with protein-assisted cell patterning. In the presence of a patterned surface with DNP moieties attached, previous studies have shown that A488-IgE sensitized RBL cells display a clustering of IgE bound FcERI receptors above patterns prepared using the parylene lift-off method. Here, an assay was prepared to demonstrate the ability of Imprint Resist 1 to pattern DNP-bound proteins such that cells were not deterred from interacting with the proteins. A single protein array of Cy3-Cy5 labeled DNP-BSA was patterned onto an aminosilanized wafer surface with Imprint Resist 1 as described in the Methods section. RBL-2H3 mast cells, sensitized with A488-IgE, were allowed to settle onto the wafer surface for several minutes before undergoing fixation and imaging. As shown by FIG. 9, sensitized RBL-2H3 cells did attach to the silicon surfaces on or near the patterned DNP-BSA. Furthermore, the A488-IgE-receptor complexes were found to cluster over the patterned features, consistent with previous studies.

Discussion

While the use of UV radiation is not required for imprint lithography, the technique typically uses harsh resists and developers much like photolithography methods, which can easily damage and denature biomolecules. In the present invention, the harsh processing conditions are replaced with our benign fluorinated Imprint Resist 1 and unreactive hydrofluoroethers as processing solvents.

Traditional imprint lithography requires a moldable resist, such that it "flows" into the recesses of the imprint stamp during imprinting and releases from the stamp after imprinting. Imprinting occurs through applied pressure of the stamp and heating of the resist. Typically, samples are significantly heated, to temperatures above the glass transition temperature ($T_g$) of the resist material. However, for biomolecule patterning applications, significant heating would damage and denature the proteins and DNA. Therefore, imprinting temperatures were kept at or below 50° C. This temperature was empirically identified as high enough to form imprint patterns, yet low enough to cause no observable adverse effects to the proteins. In order to identify the optimal set of processing conditions, several parameters were varied and tested, including temperature, pressure, length of time imprinting, resist thickness, and surface treatments of both the stamp and substrate (data not shown). Temperature values of 30° C., 40° C. and 50° C. and pressures of 100 psi, 200 psi and 300 psi were investigated, as well as imprint times of 1 minute, 2 minutes, 3 minutes and 5 minutes. Imprinting at 50° C. and 300 psi for 5 minutes gave the highest feature relief (ca. 200 nm). The effect of varying the resist thickness from 400 nm to 600 nm and 900 nm was also examined. The relief magnitude did not noticeably change with differing resist thicknesses. Therefore, 600 nm was arbitrarily selected for the processing condition set.

Finally, different surface treatments for both the stamp and substrate were investigated, including (1H,1H,2H,2H-Perfluorooctyl)Trichlorosilane (FOTS), oxygen plasma treatment, and untreated silicon with a native oxide. For both the stamp and substrate, it was determined that the untreated surfaces often exhibited a "peeling" effect during imprint, as most features were "peeled" out from the resist layer to produce patterns which were clean to the substrate and without the residue that is common in imprint lithography. In these cases, the feature relief is ca. 600 nm for a ca. 600 nm thick resist film. Traditionally, patterns are stamped into the imprint resist layer to give a degree of feature relief. The resist is then anisotropically etched to remove the remaining resist residue in the thinner regions to produce patterns, which are clean to the substrate. Following imprint at 50° C. and 300 psi for 5 minutes, samples were anisotropically etched with $Ar/O_2$ plasma (Ar: 85%, $O_2$: 15%) for 5 minutes at an etch rate of approximately 100 nm/minute, to give a final resist thickness of ca. 100 nm. $Ar/O_2$ etching exhibits a lower etch rate than with $O_2$ alone; therefore, $Ar/O_2$ etching was selected to enable a greater degree of control in determining the final resist thickness post-etching. Samples of Imprint Resist 1 post-imprinting and post-etching are shown in FIG. 2.

Both Imprint Resist 1 and the hydrofluoroether solvent were demonstrated to be benign to biomolecules in that they did not significantly deteriorate the proteins' and DNAs' binding capacities (FIGS. 3-5). Varying concentrations of streptavidin, a robust and well-known protein, were liberally exposed to Imprint Resist 1 and hydrofluoroether solvent under conditions which imitate lithographic processing. The ability of streptavidin, post resist exposure, to bind biotin was experimentally measured and found to be similar to that of streptavidin without any exposure to resist or solvent (FIG. 3). This suggests that the binding capacity, and thus the structure, of the immobilized streptavidin was not significantly altered by the addition and removal of Imprint Resist 1. However, it was found that the samples treated solely with hydrofluoroether solvent did produce a slight decrease (5-18%) in the binding capacity of immobilized streptavidin. This effect could be ascribed to the fact that the solvent remained in contact with the streptavidin in Set 2 wells for the whole duration of the resist application, bake, and removal to the Set 3 wells (a total time of approximately 20 minutes). In the case of Imprint Resist 1 coated streptavidin (Set 3 wells), the thick resist layer formed in the microwells was not easily removed by the hydrofluoroether solvent and may have played a protective role against the solvent effect seen in Set 2's wells. Thus, the use of Imprint Resist 1 and hydrofluoroether solvent on streptavidin did not significantly alter the protein's ability to bind to the biotin moiety.

As a more sensitive test for protein binding capacity, a similar assay was performed wherein PSA protein was bound to its antibody only after the antibody had been exposed to hydrofluoroether solvent and/or Imprint Resist 1 (FIG. 4). At low PSA standard concentrations (<1 ng/mL), the absorbance values for the control, solvent treated, and resist treated samples are similar, which suggests that the ability of the anti-PSA antibody to bind PSA has not been significantly affected. However, at higher PSA standard concentrations, 2.48 and 4.9 ng/mL, both the solvent and resist treated samples produce a slight, yet significant, decrease in absorbance values as compared to the controls. This decrease is similar to the decrease witnessed in solvent treated samples for streptavidin-biotin binding. Once again, the samples in solvent treated wells (Set 2) remained in contact with the anti-PSA antibody for the whole duration of the resist treatment to Set 3's wells (approximately 20 minutes), which may have caused the slight loss of binding between PSA and anti-PSA. An easier removal of Imprint Resist 1 in this assay, and hence a loss of the resist's protective function against the solvent, may explain the slight loss in absorbance values for the resist treated data.

For both assays, control sets were tested for each set of conditions in parallel with the solvent and resist treated sets. These positive control sets were not exposed to either Imprint Resist 1 or hydrofluoroethers, but instead remained in buffer solution for the treatment time durations. In addition, negative control sets were also performed so as to ensure that the fluorescent signal obtained did correlate with actual moiety and/or protein binding and was not simply due to nonspecific adsorption of the fluorescently labeled compound. The negative controls for the streptavidin-biotin binding assay are shown in FIG. 3, whereas the negative control values for the PSA antigen-antibody binding assay were subtracted from the experimental data shown in FIG. 4. Thus the fluorescent signals obtained from each experimental set are indeed due to the specific binding of the biotin moiety or PSA protein.

The sensitivity of hydrofluoroethers and Imprint Resist 1 on DNA binding was also investigated in the form of an annealing test between two complementary strands of DNA (FIG. 5). Whether treated with positive control buffer, hydrofluoroether solvent, or Imprint Resist 1, the complementary target DNA strand was able to bind to the immobilized probe DNA strand in all three instances. Furthermore, the fluorescence intensity appears to be similar in all three conditions with no one treatment condition causing a large visible decrease in target DNA fluorescence intensity. This suggests that ssDNA is not significantly affected by the solvent and resist materials or by the treatment conditions. Additional negative control tests were also performed wherein the streptavidin linker protein or the biotinylated-DNA probe were omitted from the assay. In both instances, the fluorescently-labeled target DNA strand was unable to bind to the patterns. Thus, the binding between the complementary DNA strands was found to be specific and all target DNA strand fluorescence signal measured was from specific DNA-DNA binding.

An advantage of this patterning method over those used previously is the design for multicomponent patterning. The method of the present invention makes possible the fabrication of a biomolecule array with as many patterned layers as desired. To validate this claim, an assay was performed to determine the effects of repeated lithographic processing onto biomolecules that were previously deposited. A layer of biotinylated-BSA protein was first adsorbed onto a wafer surface before undergoing multiple cycles of Imprint Resist 1 application and removal. In total, the resist was applied and removed ten separate times to simulate the conditions required to fabricate a complex multi-protein patterned array. The stability of the biotin-BSA protein was then tested by its binding to a fluorescently labeled streptavidin protein after several rounds of resist application and removal. As shown in FIG. 6, the stability of the protein over the course of ten cycles did not vary greatly, indicating that previously deposited biomolecules are not significantly damaged by undergoing multiple rounds of our imprint patterning technique. A negative control using non-biotinylated BSA validated the fact that the fluorescent signal measured during the experiment was from streptavidin binding specifically to a biotin moiety on the wafer surface and not from nonspecific binding of the streptavidin protein.

To further demonstrate our resist and technique's capability for fabricating multi-protein patterns, a schematic of the fabrication process (FIG. 7) and sample arrays are shown. The fabrication of single-protein, two-protein, and three-protein arrays are presented in FIG. 8. Bio-specific interactions between proteins and biomolecules, such as biotin binding avidin, DNP binding to anti-DNP IgE, and species specific antigen-antibody binding were relied on to detect for each distinct protein. Images of each fluorophore were taken on separate channels in the microscope and then merged to produce the images provided in FIGS. 8C and 8D. It should be noted that on occasion, small amounts of residual resist did remain on the wafer following final resist removal. These spots typically occur on or close to the locations of our alignment marks on the imprint stencil. The extremely close proximity of these lines to one another in addition to repeated imprinting directly onto these marks sometimes makes it difficult to remove all of the resist from that area. In the case of FIG. 8D, residual resist remained following the final resist removal. The labeling fluorophores bound nonspecifically to the residual resist and can be seen as small spots and streaks located between the protein patterns in the figure.

The ability to pattern cells is of enormous importance, in particular for tissue engineering applications as well as fundamental cell studies. Here, cell surface responses on patterned surfaces were investigated to determine the biocompatibility of this patterning method with living cells. RBL-2H3 mast cells were settled onto a surface of patterned DNP-BSA protein, which was patterned using Imprint Resist 1 and hydrofluoroether solvents. Following fixation and imaging, it was determined that the cells showed no signs of abnormal behavior or morphology, such as visible duress or apoptosis. Furthermore, the cells elicited a classical response of IgE-receptor clustering over the DNP patterns. These results suggest that any residual polymeric resist or hydrofluoroether solvents left behind on the patterned silicon surface do not deter cell adhesion or response. In fact, the lower panel of FIG. 9 reveals a clustering of IgE-receptors above a spot of DNP-BSA labeled residual resist, further showcasing the cell's indifferent response to the resist. Taken together, this indicates that the processing conditions for this imprint patterning method are also biocompatible for protein-assisted cell patterning, which suggests its use in fabricating multi-protein patterns for more complicated fundamental cell studies.

Although imprint patterning has distinct advantages for biomolecule patterning, including high-resolution, relatively low-cost and absence of UV radiation, this patterning method is being developed. The adaptation of a more established patterning method, for example photolithography, to biomolecule patterning would be very useful. By using a positive-tone biocompatible photoresist and hydrofluoroether solvents, biomolecules could still be patterned without direct UV exposure. Furthermore, because an etching step would not be necessary with photolithography, a single APTMS layer could be deposited at the beginning of the fabrication process, instead of after each imprinting step, thereby simplifying the patterning process.

A new concept in biomolecule patterning has been described. A highly-fluorinated polymer resist, processable in non-toxic hydrofluoroether solvents, was designed and synthesized. This polymer was shown to be patternable by imprint lithography, producing feature sizes down to 1 Both the resist and hydrofluoroethers were then demonstrated to be largely benign to biomolecules, including proteins and DNA, and suitable for use with RBL-2H3 cell surface studies. This imprint resist system was further used to pattern single-protein, two-protein, and three-protein patterned arrays of DNP-BSA, biotin-BSA, and rabbit IgG with feature sizes ranging from 1 µm to 100 µm, which demonstrates the potential of this resist for multicomponent patterning. In addition, it has been shown that undergoing multiple cycles of lithographic processing, up to ten in this instance, had negligible effects on the biomolecules deposited previously. While a three-protein array is the most complex array shown, in theory, this method makes possible the fabrication of a biomolecule array with as many patterned layers as desired. Yet more importantly, the success of this patterning method demonstrates a new paradigm in multicomponent biomolecule patterning that avoids many of the problems associated with more traditional lithographic techniques. By using benign resists and processing solvents, the common obstacles in multicomponent biomolecule patterning, including loss of biomolecule functionality and non-specific binding, are removed. Furthermore, multicomponent biomolecule arrays may be patterned in a straightforward manner through high-resolution, high-throughput and well-established lithographic patterning methods.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for making a pattern of biomolecules selected from the group consisting of peptides, polypeptides, proteins, polynucleotides and combinations thereof comprising the steps of:
   a) forming a pattern of a fluorinated organic material on a surface of a substrate such that a first portion of the substrate is covered by the fluorinated organic material and a second portion of the substrate is not covered by the fluorinated organic material;
   b) depositing the biomolecules on the patterned substrate from a) thereby associating the biomolecules with at least the second portion of the substrate, wherein the biomolecules directly contact the fluorinated organic material in the first portion of the substrate; and
   c) removing the fluorinated organic material and the biomolecules from the first portion of the substrate thereby forming a pattern of the biomolecules associated with the substrate, wherein the biomolecules exhibit at least one biological activity.

2. The method of claim 1, further comprising the step of repeating steps a), b) and c) to generate a plurality of patterns of the biomolecules on the substrate.

3. The method of claim 2, wherein the repeating step is carried out from 1 to 10 times.

4. The method of claim 1, wherein the substrate is a silicon substrate, glass substrate, an optical glass substrate or a flexible substrate.

5. The method of claim 1, wherein the fluorinated organic material has at least 25% by weight fluorine.

6. The method of claim 1, wherein the fluorinated organic material is a fluorinated organic polymer.

7. The method of claim 6, wherein the fluorinated organic polymer has the following structure:

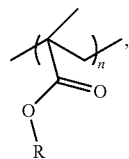

wherein R is a $C_1$ to $C_{20}$ fluorinated alkyl group and n is an integer from 50 to 2000.

8. The method of claim 1, wherein the fluorinated organic material comprises a fluorinated organic molecule having the following structure:

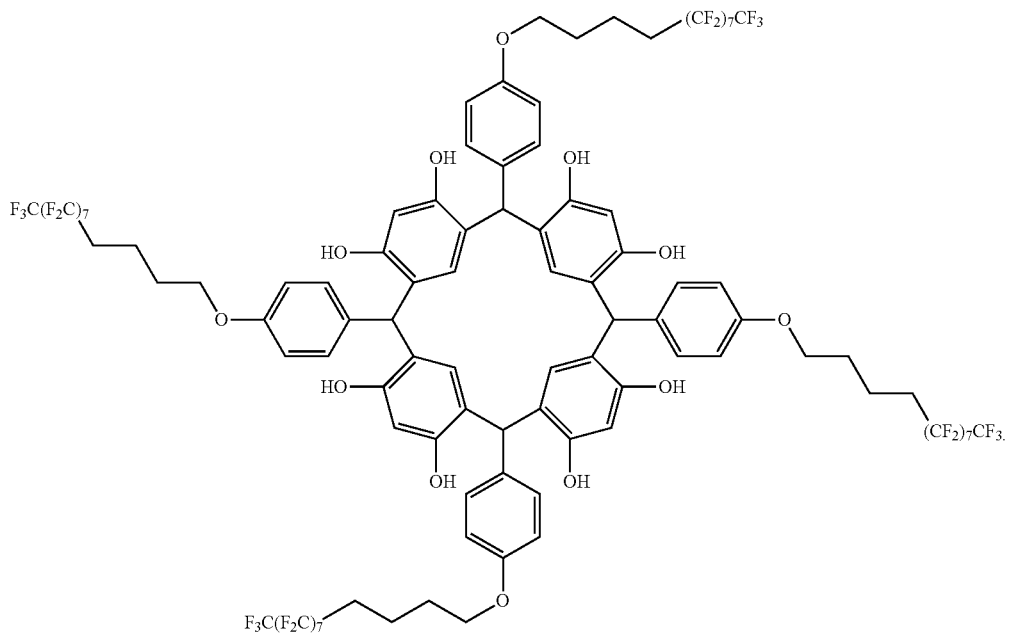

9. The method of claim 1, wherein the fluorinated organic material is deposited by spin-coating using a solution of the fluorinated organic polymer in a fluorinated organic solvent.

10. The method of claim 1, wherein the forming a pattern step a) is carried out by imprint lithography or photolithography.

11. The method of claim 1, wherein the biomaterial is a protein.

12. The method of claim 11, wherein the protein is an antibody or antigen binding fragment thereof.

13. The method of claim 11, wherein intact cells or cell extracts are deposited on the protein after deposition of the protein.

14. The method of claim 1, wherein the fluorinated organic material and the associated biomolecules are selectively removed from the substrate by contacting the substrate from step b) with a fluorinated solvent.

15. The method of claim 14, wherein the fluorinated solvent is a hydrofluoroether.

16. The method of claim 1, wherein the pattern is formed by imprint lithography and the substrate from step a) is contacted with an argon/oxygen plasma to remove residual fluorinated organic material that is not part of the pattern of fluorinated organic material.

17. The method of claim 1, wherein the forming a pattern step a) is carried out by electron beam lithography.

\* \* \* \* \*